US006468732B1

(12) United States Patent
Malin et al.

(10) Patent No.: US 6,468,732 B1
(45) Date of Patent: Oct. 22, 2002

(54) METHOD AND LONG-TERM STABLE BICARBONATE-CONTAINING DILUENT COMPOSITION, AND STORAGE MEANS THEREFOR, FOR REDUCING OR REVERSING AERATION INDUCED CELL SHRINKAGE AND STORAGE INDUCED CELL SWELLING OF A WHOLE BLOOD SAMPLE

(75) Inventors: Michael J. Malin, Park Ridge, NJ (US); Leonard Ornstein, White Plains, NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/819,263

(22) Filed: Mar. 28, 2001

Related U.S. Application Data

(62) Division of application No. 09/542,397, filed on Apr. 4, 2000, now abandoned.

(51) Int. Cl.[7] .......................... A01N 1/02; G01N 27/26; G01N 31/00; C12R 1/00; C12R 3/00
(52) U.S. Cl. .............................. 435/2; 204/401; 435/1; 435/4; 435/5; 436/17; 436/18
(58) Field of Search .............................. 204/401; 435/1, 435/2, 4, 5; 436/17, 18

(56) References Cited

U.S. PATENT DOCUMENTS

| 4,786,394 A | * | 11/1988 | Enzer et al. ................. 204/401 |
| 5,284,771 A | * | 2/1994 | Fan et al. ...................... 436/10 |
| 5,529,833 A | * | 6/1996 | Speer et al. ................. 428/215 |
| 6,040,132 A | * | 3/2000 | Wiggins ........................ 435/2 |

* cited by examiner

Primary Examiner—Christopher R. Tate
Assistant Examiner—Kailash C. Srivastava
(74) Attorney, Agent, or Firm—Morgan & Finnegan, L.L.P.

(57) ABSTRACT

The invention provides a bicarbonate-containing, crosslinker-free reagent composition which reverses and/or reduces sample handling effects, such as aeration-induced shrinkage and storage-induced swelling of cells in a whole blood sample, particularly for a blood sample requiring repeated sampling and/or subjected to long-term storage. The reagent composition serves as a diluent medium for a blood sample, or an aliquot or portion thereof. The pH of the reagent is in the range of about 7.2 to about 7.5, preferably 7.3. The stability of the pH 7.2–7.5 bicarbonate-containing reagent over time is maintained by storing the reagent in a flexible collapsible container which is impermeable to carbon dioxide and is comprised of a multilayered flexible material, preferably plastic, and attachable to a hematology analyzer.

27 Claims, 3 Drawing Sheets

METHOD AND LONG-TERM STABLE BICARBONATE-CONTAINING DILUENT COMPOSITION, AND STORAGE MEANS THEREFOR, FOR REDUCING OR REVERSING AERATION INDUCED CELL SHRINKAGE AND STORAGE INDUCED CELL SWELLING OF A WHOLE BLOOD SAMPLE

This application is a divisional application of U.S. Ser. No. 09/542,397, filed Apr. 4, 2000, now abandoned

FIELD OF THE INVENTION

The present invention relates generally to stable reagent compositions, and storage containers therefor, for use as blood diluents and for assaying blood cells and platelets in an aliquot of a whole blood sample. The invention further relates to the long-term storage of such reagent compositions in packaging designed to maintain MCV-assays of blood samples aeration-insensitive and to maintain reagent stability over time.

BACKGROUND OF THE INVENTION

The analysis of blood samples using semi-automated and fully-automated hematology analyzer instruments requires the use of specialized reagents in which blood samples are mixed and diluted. Such reagents allow the practitioner to obtain accurate, sensitive and precise measurements of a variety of blood cell parameters and to analyze the different blood cell types in a blood sample. As a particular example, hematology analysis of blood cells, especially red blood cells, platelets and reticulocytes, on automated instruments frequently involves the use of reagents comprising components which have limited stability overtime in storage.

For the analysis of blood samples containing red and white blood cells and platelets, blood samples are routinely drawn into containers (e.g., glass tubes and the like) for subsequent use and/or storage. When a blood sample is to be analyzed or tested, the container carrying the blood sample is opened and the sample is, in turn, exposed to the air. As a rule, venous blood contains about 100 times more dissolved carbon dioxide (as bicarbonate) than is present in the air. This is because red blood cells carry metabolic waste carbon dioxide from tissues to the lungs. When the container housing a venous blood sample is opened, the blood sample begins to be aerated and the surface of the red blood cell begins to be exposed to air-saturated plasma. This results in a driving force for the cells, i.e., red blood cells, to unload carbon dioxide to the air. Carbon dioxide diffuses out of the red cell membrane causing a measurable decrease in intracellular bicarbonate, and therefore, a decrease in osmolality. The cell simultaneously loses water to maintain the original osmolality. As a result, the cell shrinks during aeration. This is known as a sample handling "aeration effect". (Dacie and Lewis, Practical Haematology, fifth edition, p.38, Churchill Livingstone, 1975). With repeated blood samplings in air, the red blood cell MCV decreases and the sample handling effect is evidenced such that about 2–5% of the sample's red blood cell volume is lost in a fully aerated sample of venous blood.

Virtually all hematology methods using conventional reagents and analyzer instrumentation are susceptible to the problem of sample handling effects, in which aeration of a blood sample induces red cell shrinkage, known as aeration-induced mean cell volume (MCV) shrinkage. The extent of such MCV shrinkage can be as high as 5%. As a blood sample is sampled repeatedly for various assays and mixed, the headspace (i.e., the volume of air above the blood) in the sample storage tube increases. As the tube is opened, there is contact between air and the plasma surrounding the blood cells in the sample, which can have a detrimental effect on the blood sample, particularly after repeated uses. The severity of such a sample handling aeration effect increases if the sample is sampled repeatedly with frequent remixing and opening of the tube to the air.

In addition to the above-described sample handling effect, another serious problem related to blood sample analysis is the problem of storage effect, which is also detrimental to the integrity and quality of the cells in a stored blood sample. Indeed, the actual storage of whole blood samples in closed containers (e.g., tubes) at room temperature for 24 hours may cause the MCV to increase as much as 7%, due to the metabolism of both the red and white blood cells in the closed container of blood. The metabolism leads to the accumulation of carbon dioxide and other osmotically active products which tend to increase the internal osmolality of the cells, thereby producing swelling during storage.

More specifically, to provide a theoretical mechanism not intended to be in any way limiting, during the storage of whole blood, carbon dioxide ($CO_2$), a major metabolic product, diffuses from the white blood cells into the plasma and then into the red blood cells. Once inside the red cells, carbon dioxide is enzymatically hydrated to carbonic acid, which then dissociates to an osmotically active bicarbonate ion and a buffered proton. The dissociation is forced by the difference between the intracellular pH of the cell (approximately pH 7.4) and the $pK_{a1}$ of carbonic acid. As a result of these steps, cellular osmolality increases. Water therefore simultaneously enters the red cells to restore the original internal osmolality of approximately 290 milliOsmoles/kg, to match the extracellular osmolality, and the cells swell. Carbon dioxide, which is generated within red cells, produces a similar effect. Storage of whole blood for 24 hours at room temperature (i.e., approximately 25° C.) causes an approximately 5–7 fL (femtoliter) increase in MCV, at least part of which is due to the described process.

Thus, a goal of the present inventors was to develop reagents, which are stable over time, for use in blood sample analysis. The reagents of the present invention can reverse, decrease, or eliminate the above-described sample handling and storage effects on blood cells, i.e., by reducing aeration-induced-shrinkage or swelling from storage at room temperature. Correlative to this goal is the added need for novel storage devices and materials which provide storage packaging that maintains the stability of the newly developed reagents. Long-term stability provides considerable economic advantages to those in the art, since such reagents can be used, stored and re-used for longer periods of time before new reagents need to be purchased and used. In addition, stability of the reagent components over time is required to provide assurance to the user that the results obtained after use of the reagents with cells in hematology analysis will remain accurate, sensitive and precise following repeated use and long-term reagent storage.

Prior to the present invention, bicarbonate-containing reagents, e.g., blood diluents, that partially or completely reversed the effects of sample handling, e.g., aeration-induced MCV shrinkage, were not described. The art also fails to describe flexible, collapsible $CO_2$ barrier packaging for such bicarbonate-containing diagnostic reagents, particularly for the purposes of long-term storage of such reagents, for hematology cell analysis and measuring the properties of red blood cells and other blood cells in a whole blood sample.

To address shrinkage of MCV due to aeration of blood, Bryner et al., (1997, "The Spun Micro-Hematocrit and Mean Cell Volume are Affected by Changes in the Oxygenation State of Red Blood Cells", *Clin. Lab. Haem.*, 19:99–103), proposed fully oxygenating blood samples by treatment with an equilibrating gas mixture containing oxygen, carbon dioxide and nitrogen and the use of a layer of mineral oil in the tube as a barrier to the loss of both oxygen and carbon dioxide from the blood samples equilibrated with the gas mixtures. However, because both gases are more soluble in mineral oil than in water, mineral oil is a very poor barrier for these gases. Another drawback of the approach proposed by Bryner et al. is that their treatment of opened tubes of blood with the equilibrating gas mixture is both time consuming and a potential biohazard. The approach of Bryner et al. involves the bubbling of air through blood which generates aerosols when the bubbles break. If the blood sample should contain pathogenic agents or substances, such aerosoling could be harmful to the handler, or others nearby, due, for example, to the inhalation of such pathogenic agent or substances.

In general, diluents employed for red blood cell analysis (e.g., Bayer H*™ RBC Diluent) typically contain a very low bicarbonate concentration because of the problem of equilibration with atmospheric carbon dioxide, $CO_2$. As an example, U.S. Pat. No. 4,971,917 to Kuroda describes a reticulocyte reagent containing 1–300 mmol/L of bicarbonate and a dye to enhance the staining of reticulocytes. This patent fails to disclose or appreciate that because $CO_2$ is highly volatile, even when the bicarbonate concentration is as low as 20 mmol/L at pH 7 to 8, loss of $CO_2$ to the air can lead to a rapid rise in pH. In addition, typical plastic reagent containers (e.g., polypropylene and polyethylene) are highly permeable to $CO_2$. Such reagents stored in such containers therefore have very limited stability. The Kuroda patent also does not disclose the development of novel reagents and special storage devices for such reagents that insure long reagent stability over time.

Other blood diluent reagents contain the fixative glutaraldehyde as well as a detergent, such as SDS. In such reagents, as described by Kim and Ornstein, 1983, *Cytometry*, 3:419–427, the lytic action of the SDS was nullified by the formation of crosslinks within the cell by the glutaraldehyde fixative. However, because glutaraldehyde-containing reagents are commonly unstable and glutaraldehyde is believed to be an environmental hazard due to its toxicity and carcinogenicity, the use of such reagents is perceived as disadvantageous.

In addition, glutaraldehyde is volatile and as a component of such reagent compositions is unstable over long periods of storage, ("Glutaraldehyde polymers in aqueous solution", *Anal. Biochem.*, 201:94–98). Also, when blood samples are diluted into or mixed with reagents containing glutaraldehyde, or other fixatives, sample handling effects are "locked in" due to the formation of the chemical crosslinks. Hence, methods employing glutaraldehyde-containing reagents tend to lock in the size of the blood cells in the tube at sampling time. However, the clinical utility of the mean cell volume (MCV) measurement would be improved if the MCV parameter reported by the hematology analyzer were closer to the in vivo MCV value of a fresh blood sample.

Until the present invention, no reagent composition that served as a blood sample diluent was able to reverse sample handling effects or to reduce sample storage effects at room temperature. By the present invention, a reagent composition is provided, and a storage container is fashioned, for long-term stability of the reagent during storage. The new reagent composition, which is free of crosslinker or fixative (e.g., glutaraldehyde) and comprises bicarbonate, surfactant as sphering agent and, optionally, a metal halide salt, can totally reverse the shrinking of cells caused by aeration and partly reverse the swelling of cells indicative of the "storage effect" by up to 50%.

Use of the new reagent as a blood diluent allows the cellular bicarbonate and carbon dioxide content to equilibrate with those of the reagent which is "matched" to venous plasma. In addition, the absence of a crosslinking agent or fixative in the reagent of the present invention allows the cell volume to be affected by the bicarbonate in the reagent. Further, the newly provided flexible, collapsible, multi-layer, carbon dioxide-barrier bag storage container for use with the reagent has sufficiently low permeability to $CO_2$ to show exceptional pH and reagent stability over time; for example, over two to three years.

Thus, the present invention provides needed solutions to the universal and significant problem of typical sample instabilities during use and storage that are encountered and lamented by practitioners in the hematology art. Since the solution to the problem requires a reagent having a relatively high concentration of $CO_2$, the barrier bag provides the required long-term stability for such a reagent, and the collapsibility prevents air influx into the bag as reagent moved.

DESCRIPTION OF THE DRAWINGS

As shown in FIG. 1, the container comprises a flexible, collapsible bag portion designed to house the reagent. The bag is fitted with and contains a hollow cylindrical connector, for example, a straw, hose, or tube, which is inserted through the top opening or neck of the bag. The neck is preferably polyethylene, but other materials are suitable. For convenience, the term straw will be used herein. The straw can be made of polyethylene. The straw or tubing length allows it to reach the bottom of the bag. The straw or hollow connector can be connected to a hematology system/analyzer after a blood diluent reagent, for example, the glutaraldehyde-free, bicarbonate-containing reagent, described herein, is placed in the bag.

The reagent is added such that there is virtually no head space in the bag. The empty collapsible and flexible bag is pressed flat to expel excess air, and then is filled, preferably by a pump, so that the bag contains the reagent with virtually no extra headspace. The reagent bag is then sealed, for example, by heat-sealing the end of the straw outside of the bag. Via the straw or tubing fitting, which extends to the outside atmosphere, the bag is attached or connected to a hematology analyzer.

On the analyzer, the reagent is primed by the use of a release valve, as known to the practitioner, and as reagent is consumed, the bag collapses with no headspace. In addition, the bag is preferably contained and supported within some type of other container, for example, an open box, preferably a cardboard box, or a housing, e.g., as is known and employed for certain hematology analyzer reagents and products packaged in thin-walled disposable containers that are connected to and used in hematology analyzer systems, particularly reagents and products that are used in large volumes for hematology analyses.

Figure 1:
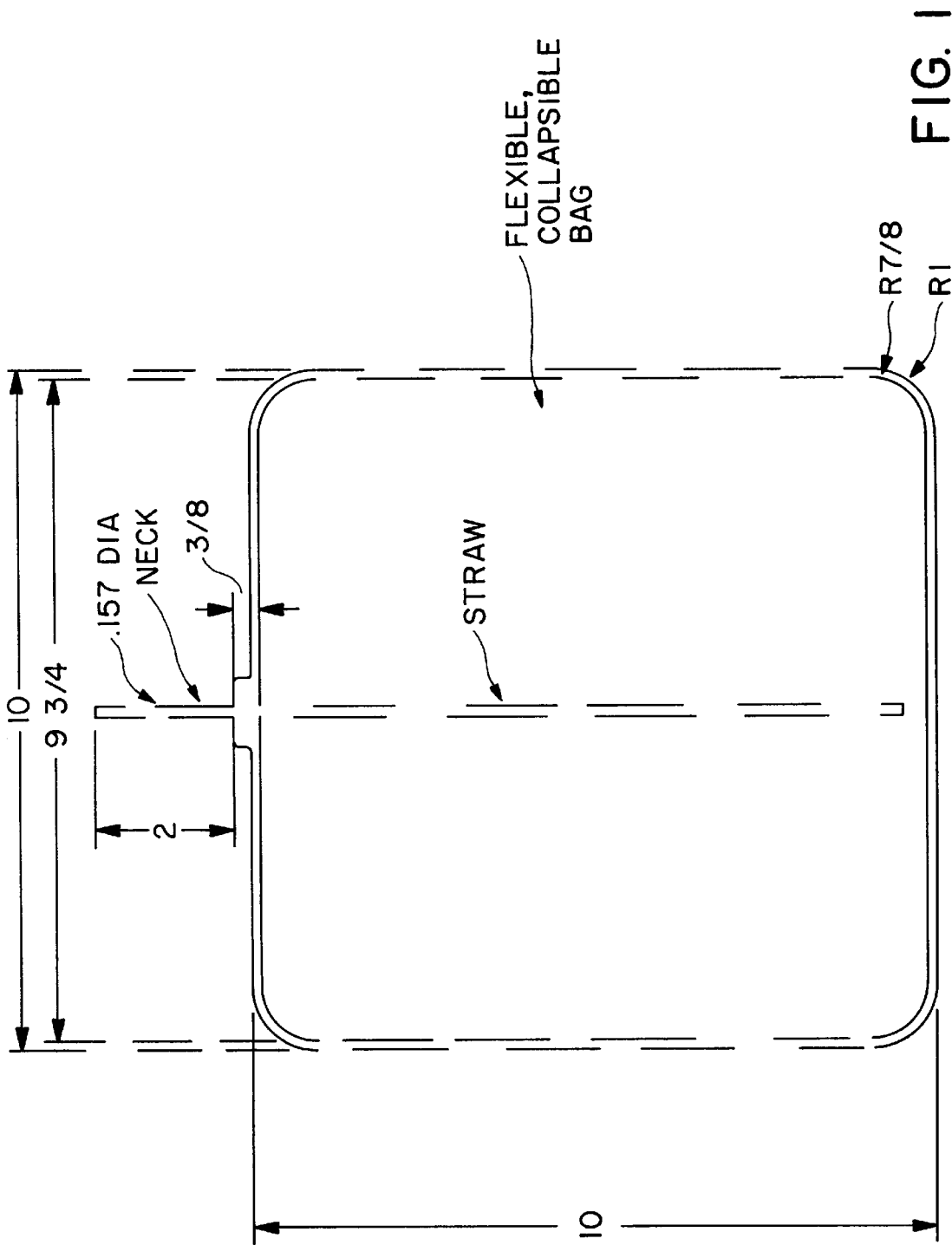
FIG. 1 shows a schematic depiction of a collapsible, multilayer, flexible $CO_2$ barrier bag, preferably plastic, for the bicarbonate-containing reagent in accordance with the present invention. For convenience, the term bag is used, although other terms such as receptacle, container, packaging are considered to be synonymous.

As depicted in FIG. 1, the collapsible flexible bag comprises double layer Saranex, having outer and inner dimensions, in inches, as shown, (Dieletrics Medistad Co., Chicopee, Mass.). All dimensions in FIG. 1 are in inches. For example, the outer dimensions of the bag in FIG. 1 are 10×10×⅞, which is suitable for holding 1 liter of reagent solution. The bag as shown is fitted with a sealed straw or tube (4 mm OD×2 mm ID), which reaches the bottom of the bag (inside) and projects about 2 inches outside as shown. However, the dimensions and storage volume of the bag, as well as the dimensions of the straw, can be empirically determined by those skilled in the art, depending on the particular need, such as the volume of reagent desired or needed to be used and stored, or the available space in and around an analyzer, and the like. Headspace in the bag would generally be approximately 1–2% of the total volume.

Figure 2:
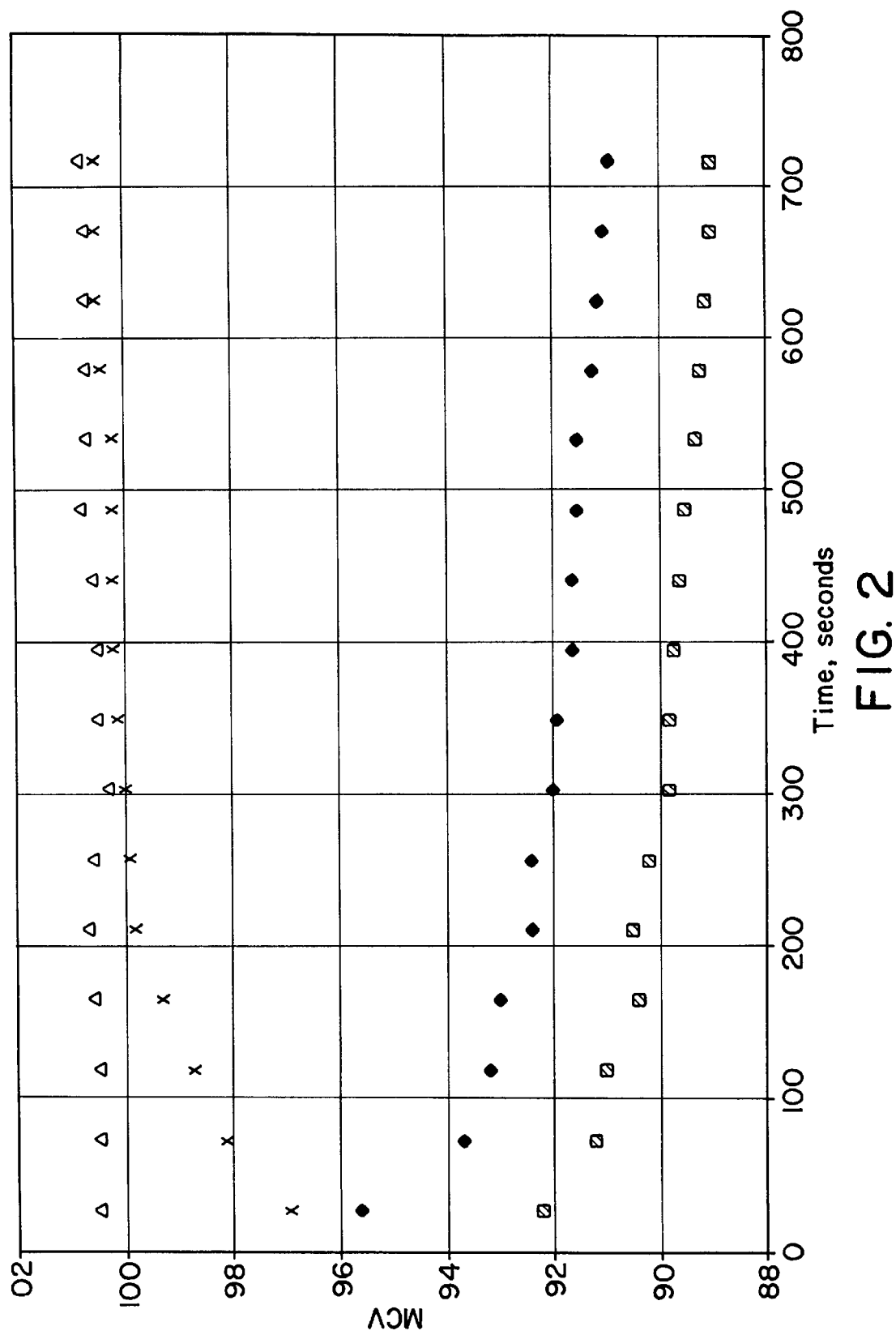

FIG. 2 shows the results of an MCV time course for venous and aerated blood sample pairs diluted 600-fold in various reagent compositions. The ♦'s indicate the MCV values of a venous blood sample mixed with Reagent 1 (RBC Diluent) containing glutaraldehyde as described herein and analyzed on the Bayer H*1™ hematology analyzer. The ■'s indicate the MCV values of an aerated blood sample mixed with Reagent 1 and assayed on the H*1™ hematology analyzer. The Δ's indicate the MCV values of a venous blood sample mixed with Reagent 2 containing laurylamido propylbetaine (LAB) zwitterionic surfactant and phosphate buffered saline (PBS), pH 7.4, 290 mOsm/kg, (no bicarbonate or glutaraldehyde), and analyzed on the Bayer H*1™ hematology analyzer. The x's in FIG. 2 indicate the MCV values of an aerated blood sample mixed with Reagent 2 and assayed on the H*1™ hematology analyzer.

Figure 3:
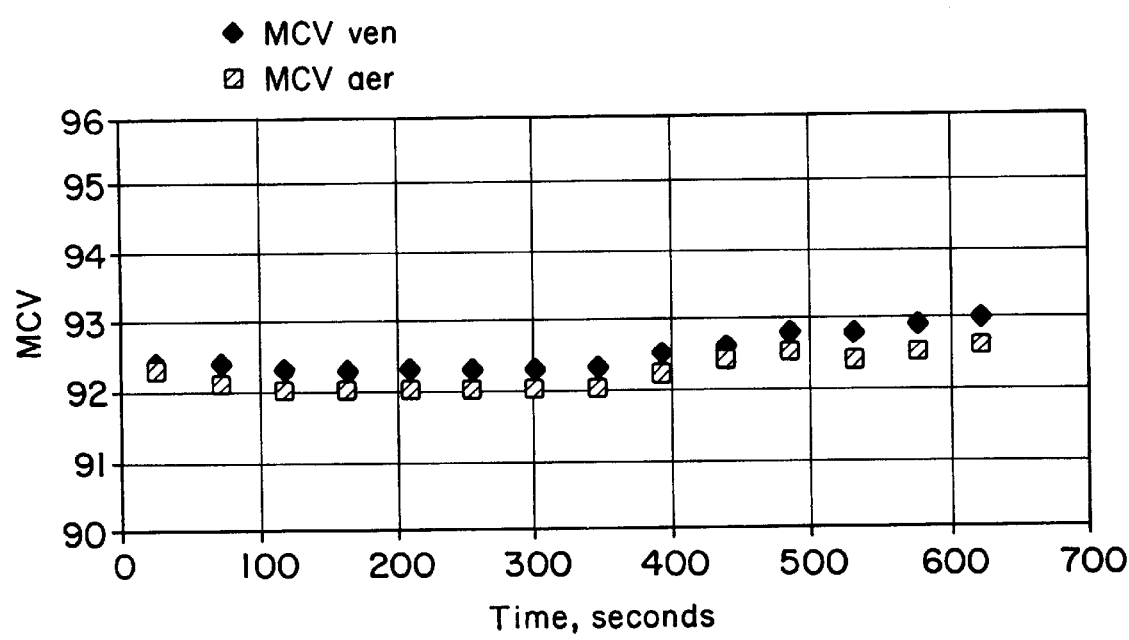

FIG. 3 shows the results of an MCV time course for venous and aerated blood sample pairs diluted in a reagent containing bicarbonate, LAB zwitterionic surfactant and PBS in accordance with the present invention. The ♦'s indicate the MCV values of a venous blood sample mixed with the bicarbonate (28 mM)-containing reagent and analyzed on the Bayer H*1™ hematology analyzer. The ■'s indicate the MCV values of an aerated blood sample mixed with the bicarbonate-containing reagent and assayed on the H*1™ hematology analyzer. An instantaneous elimination of the aeration gap is seen when the bicarbonate-containing reagent is used, compared with the results shown in FIG. 2.

SUMMARY OF THE INVENTION

It is an object of the present invention to provide stable reagent compositions for use in the analysis of blood cells, particularly, red blood cells, reticulocytes and platelets. In accordance with the present invention, the reagent compositions comprise bicarbonate and sphering agent at approximately neutral pH. Also, in accordance with the present invention, the inclusion of bicarbonate at the concentration described and its particular interactions with other components of the compositions provides stability to the compositions over time when loss of $CO_2$ to the atmosphere is prevented.

It is another object of the present invention to provide novel storage packaging for the above-described, bicarbonate-containing hematology reagent compositions, wherein the packaging affords long-term stability to the reagents stored therein by virtually preventing the loss of $CO_2$ from the reagent to the atmosphere.

It is yet another object of the present invention to provide a novel bicarbonate-containing reagent composition having long-term stability when the composition is stored in a specially-designed, flexible, multilayer $CO_2$ barrier packaging. The bicarbonate-containing reagent, in a concentration range from 28 to 1.4 mMol/L, is capable of reversing blood sample handling effects, including aeration-induced cell shrinking and swelling during use and storage. In accordance with a specific aspect of the invention, the bicarbonate-containing reagent comprising sphering agent, i.e., surfactant (e.g., n-tetradecyl dimethylammonio propane sulfonate, TDAPS, or n-dodecyl-β-D-maltoside), pH 7.3, 290 mOsm/kg stored in a flexible $CO_2$ barrier bag will completely reverse the effect of sample aeration on mean cell volume (MCV) and reverses about 50% of the overnight swelling of red blood cells in stored blood, compared with a standard, current reagent [e.g., containing glutaraldehyde and an amount of bicarbonate no more than sufficient to equilibrate with the $CO_2$ in air (e.g., ~0.1–0.2 mM)].

Further objects and advantages afforded by the present invention will be apparent from the detailed description hereinbelow.

DETAILED DESCRIPTION OF THE INVENTION

The present invention provides new hematology reagent compositions and storage packaging therefor which achieve long-ten storage stability of the reagent compositions over time and which reverse and/or reduce sample handling effects, e.g., cell shrinkage and swelling, of stored blood samples to a significant extent. The reagent compositions of the present invention are particularly suitable for use in hematology analyzer instruments for identifying, measuring and determining the properties of blood cells, particularly, red blood cells, reticulocytes and platelets. Accordingly, the reagent compositions serve as blood diluents or as matrices for blood analysis reagents, such as red blood cell and reticulocyte diluents, for mixing with whole blood samples prior to blood sample analysis.

Nonlimiting examples of particular hematology analyzers in which the reagent compositions can be beneficially employed include Bayer H*™ and Advia 120® Hematology Systems, commercially available from the assignee hereof. The reagent compositions of the present invention are particularly advantageous as reagents for red blood cell (RBC) and platelet (PLT) determinations, i.e., an improved RBC/PLT reagent, and also as a matrix for an "autoreticulocyte" reagent employed in conjunction with the Bayer H*™ and the Advia® automated hematology instruments (Bayer Corporation).

In accordance with one embodiment of the present invention, the reagent composition is an aqueous composition and preferably comprises bicarbonate, e.g., sodium bicarbonate, and a sphering surfactant. Bicarbonate is present in the composition of the invention in an amount of from about 1.4 mmol/L to about 35 mmol/L, preferably about 2.8 mmol/L to about 28 mmol/L, and more preferably about 25 mmol/L to about 28 mmol/L. Preferably, the reagent composition of the present invention contains no significant amount of glutaraldehyde, or other chemical crosslinking agent or fixative (e.g., formaldehyde, paraformaldehyde, or 1,6-hexanedial, 1,4- phthalic dicarboxaldehyde glyoxal).

The pH of the reagent composition is from about 7.2 to about 7.5, preferably, about 7.3 to about 7.4, and more preferably, about 7.3.

According to the present invention, the crosslinker/fixative (e.g., glutaraldehyde) -free, bicarbonate-containing reagent composition having a pH of about 7.2 to about 7.5 is stored in a newly-designed flexible $CO_2$ barrier bag. Such a barrier packaging as described further herein for bicarbonate-containing reagents has not been previously described, particularly with respect to reagents used to measure the volume of red blood cells.

The reagent composition of the present invention can further include an alkali metal salt, such as sodium chloride, potassium chloride, or lithium chloride, in an amount effective for maintaining the osmolality of the composition, for example, about 120 to about 150 mmol/L, preferably about 130 to 140 mmol/L. The osmolality of the complete reagent composition is about 285 milliOsmoles per kilogram (mOsm/kg) to about 295 mOsm/kg, preferably about 290 mOsm/kg.

Several general classes of zwitterionic surfactants, or nonionic surfactants, may be used as sphering agents in the reagent compositions of the present invention. The surfactant is present in the compositions in an amount effective to substantially isovolumetrically sphere the blood cells, particularly the red blood cells and reticulocytes, in the blood sample. More specifically, the surfactant is present in an amount of 7.5 mg/L to about 8.5 mg/L, preferably about 8 mg/L.

Nonlimiting examples of suitable classes of zwitterionic surfactants include betaines, including carboxybetaines, sulfobetaines (also known as sultaines), amidobetaines and sulfoamidobetaines. Of particular interest are the $C_8$–$C_{18}$, preferably $C_{10}$–$C_{18}$, alkyl betaines, sulfobetaines, amidobetaines, and sulfoamidobetaines, for example, those of the laurylamidopropylbetaine (LAB) type.

Nonlimiting examples of suitable zwitterionic surfactants in the betaine class include n-alkyldimethylammonio methane carboxylate (DAMC), n-alkyldimethylammonio ethane carboxylate (DAEC) and n-alkyldimethylammonio propane carboxylate (DAPC). Examples of the sulfobetaine class of zwitterionic surfactants include, but are not limited to, the n-alkylsultaines, or n-alkyl dimethylammonio alkyl sulfonates, such as n-alkyl dimethylammonio methane sulfonate (DAMS), n-alkyl dimethylammonio ethane sulfonate (DAES), n-alkyl dimethylammonio propane sulfonate (DAPS) and n-alkyl dimethylammonio butane sulfonate (DABS). In the "DAPS" surfactant series, TDAPS, wherein "T" is n-tetradecyl; DDAPS, wherein "D" is dodecyl; as well as hexadecyl dimethylammonio propane sulfonate, are especially suitable. TDAPS is preferred in the present invention.

The amidobetaines include, but are not limited to, n-alkylamidomethane dimethylammonio methane carboxylate or n-alkylamido methane dimethylammonio ethane carboxylate. A preferred amidobetaine is laurylamidopropylbetaine (LAB). Also suitable are the analogous amidobetaine sulfonates, such as n-alkylamidomethane dimethylammonio methane sulfonate, n-alkylamidoethane dimethylammonio ethane sulfonate and n-alkylamidopropane dimethylammonio propane sulfonate. In addition, amidobetaines which have coconut oil as their fatty acid source, e.g., cocoamidopropylbetaine (CAPB) and cocoamidosulfobetaine (CASB), may be considered for use. Further descriptions of betaines, sulfobetaines, amidobetaines and amidosulfobetaines may be found in the pertinent literature, for example, S. Takano et al., 1977, *J. Amer. Oil Chem. Soc.*, 54:139–143 and 484–486; Z. El Rossi, Cs Horvath, 1982, *Chromatographia*, 15:75–82; Kaminski and Linfield, 1979, *J. Amer. Oil Chem. Soc.*, 56:771–773.

Other zwitterionic surfactants suitable for use in the present invention include 3-[(3-cholamidopropyl)dimethylammonio]-1-propanesulfonate (CHAPS) and 3-[(3-cholamidopropyl)dimethylammonio]-2-hydroxy-1-propanesulfonate (CHAPSO).

Nonionic surfactants that are suitable for use in the present invention generally include alkylglycosides. Preferred nonionic surfactants include n-dodecyl-β-D-maltoside, n-tetradecyl-β-D-maltoside and n-tetradecyl-β-D-glucoside.

Without wishing to be bound by theory, the function of the surfactant in the reagent composition of the present invention is to sphere cells in the blood sample, particularly red blood cells and reticulocytes.

Cells are sphered so that all cells present the same orientation to the light scattering detectors. Hypothetically, the mechanism by which the bicarbonate-containing reagent acts to reverse and reduce aeration-induced cell shrinkage and closed tube storage-induced swelling of red cells is that the reagent behaves as a source of carbon dioxide that contains a $CO_2$/bicarbonate content similar to that of fresh venous plasma (i.e., 22–29 mM bicarbonate) (*Fundamentals of Clinical Chemistry*, 1st Edition, Eds. N. Tietz, W. B. Saunders, 1970, pp. 631–632). Red cells in aerated blood and "aged" red cells in room-temperature-stored blood (e.g., $\geq 24$ hours post-draw) would respectively contain less or more carbon dioxide than the bicarbonate-containing reagent. When they equilibrate with the reagent, the red blood cell volumes tend to be "restored" to the value of freshly-drawn venous blood.

A particular, yet nonlimiting, example of a hematology reagent composition of the present invention, which is particularly suitable for blood sample storage in the newly-disclosed flexible container described below, and also according to the present invention, is presented in Table 1:

TABLE 1

| Component | Amount |
| --- | --- |
| Na Bicarbonate | 25–28 mmole/L |
| TDAPS | 7.5–8.5 mg/L |
| NaCl | Effective to bring the reagent to 285–290 mOsm/L |
| pH | 7.3 (adjusted with HCl) |

The osmolality of the reagent composition exemplified in Table 1 is 290 mOsm/Kg and the pH is 7.3. The reagent composition may also contain a chelating agent, for example, ethylenediaminetetraacetic acid (EDTA), or salts thereof, or $K_3$ EDTA, and other compounds to prevent bacterial or microbial growth and/or to maintain reagent stability.

Examples of suitable anti-microbial compounds include, but are not limited to Proclin 150, I and II, (I: 2-methyl4-isothiazoline-3-one; II: 5-chloro-2-methyl-4-isothiazoline-3-one), Proclin 300, I and II and Proclin 500 (Rohm & Haas); Germall 115 (N,N'-methylenebis[N'-(1-(hydroxymethyl)-2,5-dioxo-4-imidazolidinyl] urea) (Sutton Laboratories); Dowacil 200 (1-(3-chloroallyl)-3,5,7-triaza-1-azoniaadamantane chloride) (Dow Chemical); and Bronopol (Angus Chemical Company), with Proclin 300 being preferred.

Another embodiment of the present invention encompasses the above-described bicarbonate-containing reagent composition packaged or stored in an $O_2/CO_2$ barrier bag or container designed to maintain the stability of the bicarbonate concentration of the reagent over time. It can be shown by the use of gas laws and solubility data that for the present reagent compositions having pH values of about 7.2 to about 7.5, more particularly, about 7.3 to about 7.4, the aqueous solutions are saturated with $CO_2$ at approximately 0.1–0.2 mmol/L of bicarbonate. A bicarbonate-containing composition as exemplified in Table 1 was found not to be pH-stable over time, if stored in typical glass or plastic containers (e.g., HDPE, Eagle Picher, Miami, Okla.). Such a reagent is also unstable in typical borosilicate glass because of the very slight but significant reactivity of the glass surface. Therefore, in order to maintain the bicarbonate concentration of the reagent composition near its original value, a special $CO_2$ barrier bag package or container was designed to prevent the diffusion of $CO_2$ from the reagent composition stored therein into the air.

In accordance with the present invention, if aerated blood is placed, diluted or transferred into the above-described reagent composition, the red blood cells will obtain bicarbonate from the reagent composition comprising a moderate bicarbonate concentration and will have the MCV restored to the fresh venous blood value, thereby alleviating any aeration effect as a result of sample handling.

The barrier bag (FIG. 1) was designed to be flexible and collapsible so that when it contained reagent, was installed onto and consumed by an automated hematology analyzer, such as the Bayer H*™ series and the Bayer Advia 120® Hematology System Analyzers, the bag would collapse and a gas headspace would not develop. Collapsibility and absence of headspace prevent the partitioning of $CO_2$ between the reagent and headspace gas. Thus, the bicarbonate, $[HCO_3]$, content would remain virtually constant in the reagent. Functionally, the reagent composition inside the barrier packaging is uniquely capable of completely reversing aeration-induced shrinkage of cells undergoing analysis, i.e., "MCV shrinkage". Thus, this new barrier packaging (e.g., barrier bag) can serve as a storage container for the hematology reagent compositions described herein.

The reagent barrier bag can be made of a suitable multilayer, flexible, collapsible material, for example, plastic or aluminum. A nonlimiting example of such material is that commercially available from the Dow Plastics Co. under the name Saranex 15 Plastic Film. A test reagent barrier bag in accordance with the present invention was designed by Dielectrics Medistad Company, DMC, 270 Burnett Road, Chicopee, Mass. 01020-4688.

As shown in FIG. 1, the barrier reagent storage bag was fitted with a hollow connector (e.g., a straw or tubing or hosing) which allowed connection to the appropriate port of a hematology analyzer system (e.g., the Bayer H*™ System Analyzer or Bayer Advia 120® Hematology Analyzer). The hollow connector, or plastic (e.g., polyethylene) straw, is relatively impervious to $CO_2$ and is preferably identical in length to the sleeve length of the storage bag. The reagent was loaded into the empty bag such that there was no headspace (air) in the bag. For example, loading of the reagent into the bag can be carried out with a suitably sized syringe.

The barrier bag was constructed such that the walls were comprised of double layers of Saranex 15 (Dow Plastics), 4 mils (0.004 inches) in thickness. Saranex 15 film is described as a five-layer coextruded barrier film designed for use in form-fill-seal pouches and other packaging applications. It is available as 3.0 or 4.0 mil., natural color, medium slip, also available with one side corona treatment, in widths from 6 inches to 80 inches. (Dow Plastics, "Films and Engineered Laminates", 1989, Dow Chemical Company, Midland, Mich.).

More particularly, the five layers of Saranex 15 comprise the following: LDPE/EVA/PVDC/EVA/LDPE, where LDPE represents "Low Density Polyethylene"; EVA represents "Ethylene Vinyl Alcohol"; and PVDC represents "Polyvinylidene [di]Chloride". For the purposes of the present invention, the walls of the bag were designed in the following manner: air/LDPE/EVA/PVDC/EVA/LDPE/aq. reagent/LDPE/EVA/PVDE/EVA/LDPE/air, where "air" represents the outside bag-air interface and "aq. reagent" represents the aqueous reagent composition of the present invention, which is contained within the bag.

The barrier properties of each polymer layer of the illustrative barrier storage bag are summarized in the following Table 2:

TABLE 2

| Polymer layer | Water barrier | $O_2$ Permeability ($cm^3$ mil/100 $in^2$ day atm) |
| --- | --- | --- |
| Low density polyethylene (LDPE) | excellent | 480, poor |
| Ethylene vinyl alcohol (EVA) | poor | 0.017 at 0% relative humidity; 3.0 at 95% relative humidity |
| poly(vinylidene) [di]chloride (PVDC) | excellent | 0.10 |

The barrier properties of Saranex 15 can be particularly observed from Table 2. $O_2$ permeability data are presented in the table. $CO_2$ permeability can be estimated from $O_2$ permeability, because $CO_2$ permeability is generally about 3 to 6-fold greater than $O_2$ permeability. EVA is an excellent barrier layer to $O_2$ and $CO_2$ only when protected from water. In Saranex 15, EVA is protected from water by LDPE and PVDC. As designed, the barrier bag comprises a double layer of Saranex 15 which provides enhanced protection of EVA against exposure to water. (Wiley Encyclopedia of Packaging Technology, Ed. M. Bakker, 1986, New York, N.Y., pp. 48–52).

It is to be understood that the present invention also embraces other types of collapsible flexible $CO_2$ barrier packaging (e.g., plastics and the like) which comprise materials having the properties that allow the bicarbonate-containing reagent composition, pH 7.2–7.5, to remain stable and to maintain pH over time. Accordingly, it is envisioned that aluminum or metal foil (commercially available from Corning), preferably coated with polypropylene or polyethylene, could be used to design a collapsible and flexible container having the properties suitable for use in the present invention. The barrier bag may be of any practical dimension and shape, for example, a cube (cubetainer) or rectangular. For greater durability, two or more layers of the flexible, $CO_2$ barrier material, e.g., plastic, can be used.

EXAMPLES

The following examples as set forth herein are meant to illustrate and exemplify the various aspects of carrying out the present invention and are not intended to limit the invention in any way.

Example 1

Example 1 provides Materials and Methods used in experiments to analyze and overcome sample handling and storage effects on blood samples.

Whole blood samples were obtained from volunteers at Bayer Corporation and were collected in purple-top Vacutainer™ tubes, anticoagulated with $K_3$EDTA.

Materials, Reagents and Methods
Blood Sample Aeration:

For the aeration of blood, two tubes of freshly drawn blood (<2 hours post-draw) per donor were obtained. One tube was labeled, "venous", and set aside on the bench. The contents of the other tube were poured into a 25 ml Erlenmeyer flask and a small stir bar was added. The flask was covered with an inverted 250 ml beaker which had damp paper towels packed into the bottom in order to minimize evaporation of water from the blood. The blood was stirred gently for 2–5 hours. The color of the blood changed from dark red (venous) to a brighter shade of red as aeration proceeded.

The extent of aeration could be increased by either prolonging the slow mechanical stirring or by an alternative procedure in which a clean glass pasteur pipet was repeatedly gently filled with the blood and then discharged so that the blood ran down the inner surface of the flask.

The MCV of the aerated sample was monitored on an Bayer H*™ System hematology instrument. Typical MCV changes obtained with this procedure were 3 to 5 fL smaller than the MCV of the venous control. The aerated sample was then transferred back to the original Vacutainer™ tube and sealed. Percent hemolysis due to stirring was estimated by comparing the RBC counts of the venous and aerated samples and was generally in the range of 1.5 to 1.8%.

RBC channel and other hematological data were obtained in the manual closed-tube mode on a Bayer H*3™ analyzer, which was equipped with a MCTS (i.e., a manual closed tube sampler), so that the tubes were never opened during assay. In general, for these experiments, samples were automatically mixed by inversion (20 times) every 10 minutes to counteract settling of the blood cells. The system was calibrated and standardized according to the H*3™ User's Manual, sections 12 and 13, respectively. The system was washed according to the H*3™ User's Manual. For runs which contained 3 to 5 pairs of duplicates, standard deviation (pooled over multiple donors) was calculated for RBC channel parameters with the following equation:

$$SD=[Sum\ (d^2)/2N]^{1/12},$$

where d is the difference between duplicate values obtained with a particular reagent, and N is the number of samples in the set.

Absorbance data were measured with a Cary 3 spectrophotometer and pH was measured with a Radiometer pH meter, model pHM83, which was calibrated with buffers at pH 7.00 and 10.00. The osmolality of test reagents was determined with a Fiske Freezing-Point Osmometer, model one-Ten. The osmometer response was checked with 290 mOsm/Kg control material obtained from Wescor, Incorporated, Logan Utah.

Bicarbonate Assay:

The bicarbonate concentration in test RBC diluents was determined by the following spectrophotometric method. The test reagent was diluted 100-fold with MilliQ-filtered (MQ) water which had been boiled to remove $CO_2$. Next, 1.00 ml of the diluted sample was mixed with 1.00 ml of $CO_2$ Coenzyme reagent in a covered cuvette and the absorbance at 360 nm was monitored for 1 minute at a cuvette temperature of 37° C. on the Cary 3 Spectrophotometer. One ml of $CO_2$ Enzyme reagent was added to the cuvette, and after mixing, the absorbance was monitored for an additional 14 minutes. The above-described Coenzyme and Enzyme Reagents were obtained from Intersect Systems, Inc., Longview, Wash. The rate of absorbance change was practically nil between 14 and 1 5 minutes of reaction time. The absorbance change which occurred after addition of the Enzyme reagent was corrected for the blank contribution of boiled MQ water. The method was calibrated with a Technicon (now Bayer Corporation) SETpoint $CO_2$ Calibrator with an assigned value of 30 meq/L.

The Coenzyme reagent contained AND+/NADH and the Enzyme reagent contained phosphoenolpyruvate carboxylase, $Mg^{+2}$ ions and malate dehydrogenase. The assay registered the conversion of NADH to AND$^+$, which is proportional to the bicarbonate concentration, with a corresponding loss of absorbance.

To remove the buffy coat only, sealed Vacutainers™ of blood (containing predominantly leukocytes) were placed in a Sorvall Model RC-3 Centrifuge which was equipped with a model HG4L rotor and centrifuged for minutes at 2500 rpm (ca. 680 g) at 25° C. The level of the sample meniscus was marked on the tube. The plasma supernatant was carefully removed with a Pasteur pipet and transferred to a clean test tube which was then sealed. Most of the buffy coat was removed with a Pasteur pipet. Plasma was then added back to the original volume, and the tube was resealed.

Storage of Blood Samples for Aging/Storage Experiments:

Blood samples, in sealed Vacutainer™ tubes (typically 7 ml of blood), were stored for 24 hours or 48 hours in a test tube rack with the stoppers "up". Storage temperature was either refrigerated (4–8° C.) or room temperature, RT (22–25° C.) on the bench.

Reagent Compositions:

Several reagent compositions were prepared for use and testing as blood diluent and storage media according to the present invention.

1) Reagent composition comprising PBS/TDAPS/290 mOsm/kg/EDTA, pH 7.35

To prepare this reagent composition, 900 ml of MQ water were delivered into a 1 liter type A glass graduated cylinder, and the following solutes were added and stirred until dissolved: Na Phosphate, dibasic (2.70 g); Na Phosphate, monobasic monohydrate (0.55 g); $Na_2$EDTA dihydrate (1.50 g); $Na_4$EDTA trihydrate (1.40 g); NaCl (7.11 g); Proclin 150 (0.4 ml). The osmolality was 312±0 mOsm/Kg (n=2). The osmolality was adjusted to 291±0 mOsm/Kg with 72 ml of MQ water yielding a first solution. For the working reagent: 59 μL of stock TDAPS solution (35.0 g/L) was added to 250 ml of the first solution to yield a final concentration of 8.3 mg/L. The pH was 7.26. The working reagent solution was filtered through a 0.2μ Supor membrane disc (Gelman), transferred to a 250 ml HDPE bottle and stored on the bench.

2) Reagent composition comprising PBS/TDAPS/290 mOsm/kq, pH 7.35

To prepare this reagent composition, 800 ml of MQ water were added to a 1 liter type A glass graduated cylinder. The contents of one bottle of phosphate buffered saline (PBS), (Sigma Chemical Co.) was added and stirred until dissolved. Sigma PBS is a mixture of powdered solids, which was reconstituted with 1 liter of MQ water and contains NaCl (120 mM), KCl (2.7 mM) and phosphate buffer (10 mM), pH 7.4. 0.4 ml of Proclin 150 were added. The osmolality was 317±1 mOsm/Kg. The osmolality of the solution was adjusted to 293±2 mOsm/Kg by addition of 75.4 ml of MQ water (first solution). To prepare the working reagent, 59 μL of stock TDAPS solution (35.0 g/L) was added to 250 ml of the first solution to yield a TDAPS concentration of 8.3 mg/L. The pH was 7.34. The working solution was filtered through a 0.2μ membrane disc and transferred to a 250 ml HDPE bottle and stored on the bench.

An analogous reagent containing Lauryl Amido Betaine (LAB), (obtained from Scher), instead of TDAPS was prepared by the addition of 0.020 ml of LAB solution (35.0 g/L) per 100 ml of PBS solution, pH 7.3, to provide a nominal final LAB concentration of 7.0 mg per 100 ml. [PBS: Sigma dry powder blend, to prepare 1 L containing NaCl (120 mmol), KCl (2.7 mmol), phosphate buffer salts (10 mmol)].

3) Reagent composition comprising NaHCO3/NaCl/TDAPS/290 mOsm/kq, pH 7.3

To prepare this reagent composition, 850 ml of MQ water were added to a one liter type A glass graduated cylinder. The following solutes were added, stirred until dissolved and stoppered to minimize air contact: NaCl (7.02 g); NaHCO3 (2.10 g); Proclin 150 (0.4 ml). The pH was adjusted to pH 7.3 with a few milliliters of 6N HCl. The osmolality was 323±1 mOsm/Kg; and was adjusted to 290±1 mOsm/Kg with 97 ml of MQ water to form a first solution. 59 μL of stock TDAPS solution (35.0 g/L) was added to 250 ml of the first solution to yield a final TDAPS concentration of 8.3 mg/L. 250 ml of the TDAPS-containing solution was transferred to a 250 ml glass screw-top bottle and was used immediately.

An analogous reagent containing LAB instead of TDAPS was prepared by the addition of 0.020 ml of LAB solution (35.0 g/L) per 100 ml of NaCl/NaHCO$_3$ solution, pH 7.3, to provide a nominal final LAB concentration of 7.0 mg per 100 ml. 250 ml of the LAB-containing solution was transferred to a 250 ml glass screw-top bottle and was used immediately.

Example 2

To determine the effect of aeration on MCV, the experiments described in Example 2 were performed.

As discussed hereinabove, two types of sample handling effects are known to affect MCV of blood cells: 1) shrinkage due to aeration and 2) swelling due to storage at RT. To demonstrate such effects resulting from the use of a reagent comprising glutaraldehyde and SDS (e.g., Bayer RBC/PLT H*™ System reagent), sample aeration (described in Example 1, Methods) was applied to three venous/aerated blood sample pairs that had been mixed with this RBC/PLT reagent, for example, as described by Kim and Ornstein, 1983, Cytometry, 3:419427. The mean MCV aeration-decrease using this glutaraldehyde-containing reagent was −4.8 fL (see Table 3). As observed in Table 3, no change was observed in the RBC count which showed that neither detectable evaporation of water (increase in the concentration of the blood sample) from the aerated samples nor detectable hemolysis had occurred.

TABLE 3

Effect of Sample Aeration on MCV and Other RBC/PLT Channel Parameters

| Reagent | Blood Sample: Venous/ Aerated | RBC, Count × 10$^6$ | MCV, fL | RDW, % | HDW, g/dL | PLT Count × 10$^3$ | MPV, fL | PDW, % | % Change, ΔMCV |
|---|---|---|---|---|---|---|---|---|---|
| Glutaraldehyde/ SDS | Venous (mean) | 4.95 | 93.4 | 13.1 | 2.64 | 279 | 8.5 | 48.2 | 0 |
| | SD | 0.03 | 0.04 | 0.2 | 0.01 | 14 | 0.1 | 0.4 | |
| | Aerated (mean) | 4.94 | 88.6 | 13.0 | 2.69 | 288 | 7.4 | 54.4 | 5.1 |
| | SD | 0.05 | 0.2 | 0.1 | 0.01 | 10 | 0.1 | 0.2 | |

The abbreviations used in Table 3 are as follows: SDS: sodium dodecyl sulfate; SD: standard deviation; RBC: Red Blood Cell; MCV: Mean Cell Volume (Red Cells); RDW: Red Cell Distribution Width; HDW: Hemoglobin Distribution Width; PLT: Platelets; MPV: Mean Platelet Volume; PDW: Platelet Distribution Width; % change MCV:

It should be appreciated that the "flask" method of aeration as described in Example 1 is a practical experimental procedure and facilitated the simultaneous aeration of multiple samples. However, in the hematology laboratory, sample aeration will occur when sample tubes are opened to the air and remixed. For example, during reproduction runs using a hematology analyzer, samples may be aspirated about 30 to 40 times in the open-tube mode with frequent remixing. The change in MCV associated with 30 aspirations of a full tube of blood was found to be 2.4 fL. The extent of change depends strongly on the headspace volume in the tube. Aeration is a more serious problem for samples which have a large headspace. As is well known, in vitro aeration of anticoagulated venous blood causes a 2% reduction in packed cell volume (PCV) (Hematocrit, volume percent of packed red blood cells), (Dacie and Lewis, Practical Haematology, Fifth Edition, Churchill Livingstone, 1975, p. 38).

Example 3

In this example, several reagent compositions were prepared to test and compare their ability to reduce or reverse sample handling effects, particularly the aeration effect on MCV.

The present invention has provided specific reagent compositions which effectively reverse the aeration effect on MCV. A glutaraldehyde-free reagent composition comprising about 28 mmol/L bicarbonate, an amount which closely resembles the amount of bicarbonate in venous blood (NB: the bicarbonate concentration of venous blood is 21–28 mmol/L in plasma, N. Tietz, Fundamentals of Clinical Chemistry, W. B. Saunders, 1970, p. 632), did, in fact, completely reverse the aeration effect compared with the use of a reagent comprising glutaraldehyde and SDS. In such a glutaraldehyde-free reagent, samples of venous and aerated red cells were allowed to equilibrate in test tubes with the reagent for a variable time period. The sample/reagent mixtures contained in the test tubes were aspirated as a function of time by a hematology analyzer.

Venous or aerated blood was manually diluted (600-fold) into either a RBC Diluent containing glutaraldehyde, or into a glutaraldehyde-free diluent which comprised PBS containing LAB (7.0 mg/L) as the sphering agent, pH 7.3 and 290 mOsm/Kg (with no added bicarbonate). This reaction mixture was aspirated every 46 seconds into an H*1™ hematology system for a total duration of about 600 seconds and time course curves were plotted. The time-course curves are presented in FIG. 2.

In FIG. 2, the data presented for the lower set of curves (represented by the filled squares and triangles) were obtained with the RBC Diluent containing glutaraldehyde and SDS (Reagent 1). This set maintained a roughly parallel course in which the "venous" curve was displaced from the "aerated" curve by about +4 fL. In contrast, the data for the upper set of curves (represented by the open triangles and "x"'s), were obtained with the glutaraldehyde-free reagent containing PBS/LAB (Reagent 2). The "aerated" curve rose to meet the "venous" curve after about 300 seconds of incubation time. From this point, the two curves continued on together with a small displacement.

This example illustrates that in a RBC analysis method run on a Bayer H*™ System hematology analyzer, aeration induced by sample handling, caused shrinkage of the cells which was "locked in" by the formation of chemical (glutaraldehyde) cross-links within the cell with the use of the glutaraldehyde-containing reagent. Hence, equilibration between the venous and aerated states did not occur with the reagent containing this crosslinker/fixative. By contrast, when the crosslinker was omitted, equilibration did occur, and the "aerated" curve slowly rose to meet the "venous" curve (FIG. 2). This experiment has been repeated several times with TDAPS replacing LAB and essentially the same results were obtained.

Example 4

In this Example, a blood sample was diluted 625-fold, off-line, into a reagent containing PBS/LAB/NaHCO$_3$ (28 mM), pH 7.3, 287 mosm/kg. The mixture was aspirated into the H*™ Hematology System approximately 26 seconds after mixing, and then at 46 second intervals up to about 10.5 minutes. Aerated and venous blood samples from the same donor were tested by this method and the resulting MCV time courses are presented in FIG. 3. In contrast to FIG. 2, the data set of FIG. 3 illustrates that when the reagent contained 28 mM NaHCO$_3$, the MCVs of venous and aerated blood were identical within experimental error from the outset. The MCVs obtained with the glutaraldehyde-SDS-containing reagent yielded 90.0+/−0.1 and 86.5+/−0 for the venous and aerated samples (4.5% relative difference). Thus, the PBS/LAB/bicarbonate reagent eliminated the difference in MCV caused by sample aeration. In addition, compared with the results described in Example 3, the immediate elimination of the aeration-induced MCV difference was caused by the inclusion of 28 mM bicarbonate in the reagent composition according to the present invention.

Example 5

In this Example, the performance of the glutaraldehyde-free bicarbonate-containing reagent, pH 7.3, of the present invention was compared to the performance of a standard glutaraldehyde- and SDS-containing RBC/PLT diluent on a Bayer H*™ Hematology Analyzer using a venous/aerated blood sample pair. The reagent containing bicarbonate and TDAPS, pH 7.3, replaced the RBC/PLT reagent containing glutaraldehyde/SDS in the reagent tray of the hematology analyzer, and samples were aspirated with the manual closed tube sampler. All RBC parameters are presented in Table 4. With the RBC/PLT glutaraldehyde-containing diluent, the aeration gap was 7.0 fL, (7.5% change in MCV), while with the diluent of the present invention (i.e., containing bicarbonate and no glutaraldehyde), the gap was 0 fL. The RBC count, RDW, HDW, PLT count, and MPV were comparable for both reagents.

TABLE 4

Venous and Aerated Blood Sample Pairs; RBC/PLT Reagent (Diluent) containing glutaraldehyde and SDS compared with Test Reagent Composition (Diluent) containing bicarbonate and TDAPS, pH 7.3, 290 mOsm/Kg

| Reagent (Diluent) | Blood Sample*: venous/aerated | RBC | MCV | RDW | HDW | PLT | MPC |
|---|---|---|---|---|---|---|---|
| Glutaraldehyde/SDS-containing reagent | Venous | 4.39 | 93.7 | 12.8 | 2.10 | 312 | 8.5 |
|  |  | 0.02 | 0 | 0.1 | 0.01 | 5 | 0.1 |
|  | Aerated | 4.43 | 86.7 | 12.8 | 2.16 | 322 | 7.5 |
|  |  | 0.07 | 0 | 0.1 | 0 | 11 | 0 |
| Test Reagent containing bicarbonate and TDAPS, pH 7.3; 290 mOsm/kg | Venous | 4.42 | 98.4 | 12.7 | 1.92 | 328 | 7.9 |
|  |  | 0.1 | 0.1 | 0.1 | 0.01 | 7 | 0.1 |
|  | Aerated | 4.32 | 98.4 | 12.7 | 1.90 | 334 | 7.0 |
|  |  | 0.02 | 0 | 0.1 | 0.01 | 13 | 0.1 |

*Blood sample set: 3 bloods in duplicate

The results of this experiment indicate that the aeration gap could eliminated with the use of the bicarbonate-containing reagent composition as diluent. However, as mentioned herein, the pH 7.3 bicarbonate-containing reagent was not pH-stable, unless stored in special barrier packaging in accordance with the present invention. For example, when stored in a tightly capped bottle (HDPE or glass) with little headspace, the pH of the bicarbonate-containing reagent increased to 7.76 within 24 hours.

It is hypothesized here for a theory of mechanism, while not intending to be binding on the invention presented herein, that pH instabilities of the reagent stored in HDPE and glass may be caused by different factors. In HDPE, the apparent cause is equilibration of $CO_2$ dissolved in the reagent with atmospheric $CO_2$, hydration of dissolved $CO_2$ to carbonic acid and equilibration to bicarbonate at pH 7.3. In glass, the hypothetical cause may be ion-exchange with the glass surface. If the reagent pH was readjusted to 7.3 with HCl, the described reagent function was recovered thereafter. This suggests that reagent function is retained despite some loss of $HCO_3^-$ from the reagent to the air as $CO_2$.

Because the hydration of dissolved $CO_2$ to carbonic acid requires about 24 hours to reach equilibrium, it is appropriate to allow for this when the reagent is formulated.

After multiple observations of pH drift with fresh preparations of this reagent that had been stored in glass or HPDE plastic containers, the present invention was discovered to provide a solution to the fundamental problem of pH instability of the reagent upon storage. Accordingly, pH-stabilization of the bicarbonate-containing reagent composition was achieved by the design and use of a carbon dioxide-barrier bag. Experiments to demonstrate the efficacy of this approach involved monitoring the constancy of reagent pH over a period of months in various storage containers, such as in the multilayer bag described herein. See Example 12 below.

Example 6

The experiments described in this example and summarized in Table 5 were carried out to compare the performance of a glutaraldehyde-and SDS-containing reagent (i.e., H*™RBC Diluent, Reagent A) with that of the bicarbonate-containing, glutaraldehyde-free reagent, pH 7.3, of the present invention (Reagent B), for their effectiveness in reversing the swelling of red blood cells in stored whole blood samples. More specifically, Reagent B comprised 8.3 mg/L TDAPS, 29 mM NaHCO$_3$, 289+/−1 mosm/kg, pH 7.3.

Three tubes of venous blood from each of three donors were obtained. On Day 1, the three blood samples were assayed using each of the reagents and the MCVs were recorded. The sample tubes were allowed to stand on the bench for 24 hours, then the samples were re-assayed on Day 2. The percent reversal of storage induced swelling was calculated.

TABLE 5

Reversal of Storage-Induced Swelling of Red Blood Cells in Whole Blood. Comparison of Reagent of the Present Invention Comprising Bicarbonate/TDAPS/pH7.3/290 mosm/kg (No Glutaraldehyde) With Reagent Composition Containing Glutaraldehyde and SDS (H* ™ RBC Diluent)

|  | Blood Sample* blood 11 | Blood Sample blood 13 | Blood Sample blood 15 |
| --- | --- | --- | --- |
| Reagent A: Glutaraldehyde-containing Reagent Composition (H* ™ RBC Diluent) | | | |
|  | MCV, fL | MCV, fL | MCV, fL |
| Day 1 | 89.3 | 87.2 | 86.2 |
|  | 0.1 | 0.2 | 0.1 |
| Day 2 | 95.4 | 92.4 | 91.8 |
|  | 0.1 | 0.4 | 0.2 |
| MCV change, fL | 6.1 | 5.2 | 5.6 |
| MCV % change | 6.8% | 6.0% | 6.5% |
| Reagent B: Bicarbonate (29 mM)/TDAPS/pH7.35/289 mosm/kg Reagent (No Glutaraldehyde) | | | |
|  | MCV, fL | MCV, mL | MCV, fL |
| Day 1 | 95.8 | 94.5 | 93.1 |
|  | 0.1 | 0.1 | 0.1 |
| Day 2 | 99.4 | 97.0 | 95.9 |
|  | 0.1 | 0.2 | 0.1 |
| MCV change, fL | 3.6 | 2.5 | 2.8 |
| MCV % change | 3.8% | 2.6% | 3.0% |
| Calculation of Effective % Reversal of Swelling by Glutaraldehyde-Free Reagent With Respect to H* ™ RBC Diluent** | | | |
| % reversal by glut-free HCO$_3$ reagent | 44% | 57% | 54% |
| % reversal by H* ™ RBC Diluent*** | 0% | 0% | 0% |

*Blood sample set: 3 replicates per data point.

In Table 5:

Calculation of effective % reversal of swelling by glutaraldehyde-free reagent according to the present invention:

(%MCV Increase with H*™RBC Dil−%MCV Increase with Glut-Free Dil)/% MCV Increase with H*™RBC Dil×100

Glutaraldehyde-containing H*™RBC Diluent was defined to cause 0% reversal of storage-induced swelling.

Example 7

In this Example, the characteristics of a reagent containing PBS/pH 7.3/290 mosm/kg/TDAPS (with no added bicarbonate) were compared with those of a reagent containing glutaraldehyde/SDS/290 mosm/kg/pH 7.3, with respect to the abilities of these reagents to reverse sampling handling effects.

Three tubes of blood from one donor were obtained. One tube was aerated by the method described in Example 1. The second tube was labeled "Venous Day 1", and the third tube was labeled "Venous Day 2", and was stored (stopper up) on the laboratory bench for 24 hours.

On Day 1 (the blood was less than 8 hours post-draw), the aerated and venous "Day 1" tubes were assayed on the H*1™ Hematology System with both reagents using the manual closed tube samples. On Day 2 (24 hours later), the Venous Day 2 sample was assayed with both reagents. The results are summarized in Table 6.

The results indicate that the glutaraldehyde-free reagent allows 36% reversal of the aeration effect and 20% reversal of the 24 hour storage effect.

Example 8

The experiments in Example 8 were performed to compare the glutaraldehyde-free, bicarbonate-containing reagent of the present invention with a glutaraldehyde/SDS-containing reagent with respect to the reversal of swelling due to sample aging.

In these experiments, two tubes of venous blood were obtained from three donors. These were labeled "Day 1" and "Day 2". On Day 1, one tube was assayed on the H*1™ Hematology System and the other tube was stored on the laboratory bench with the stopper up. Twenty-four hours later, the Day 2 tube was assayed. The MCV results are summarized in.

TABLE 6

SUMMARY OF RBC/PLT CHANNEL PERFORMANCE WITH AERATED AND STORED BLOOD SAMPLES

| Reagent | Day | Sample* | RBC | MCV | CHCM | RDW | HDW | PLT | MPV | PDW | Aeration Induced ΔMCV, fL | % Change Aeration | % Reversal of Aeration | Storage Induced ΔMCV fL | % Change Swelling | % Reversal of Swelling |
|---|---|---|---|---|---|---|---|---|---|---|---|---|---|---|---|---|
| 1) Glut/ SDS, (290 mosm/kg) | 1 | VEN | 4.85 | 88.1 | 32.9 | 13.4 | 2.65 | 308 | 7.6 | 49.9 | 4.7 | 5.3 | 0 | | | |
| | | SD | 0.02 | 0.1 | 0.1 | 0 | 0 | 8 | 0.2 | 0.8 | | | | | | |
| | 1 | AER | 4.89 | 83.4 | 35.5 | 13.2 | 2.69 | 316 | 6.6 | 54.8 | | | | | | |
| | | SD | 0.12 | 0.1 | 0 | 0.1 | 0.01 | 9 | 0.1 | 0.2 | | | | | | |
| | 2 | VEN | 5.00 | 92.9 | 30.4 | 13.8 | 2.65 | 306 | 6.4 | 54.7 | | | | 4.8 | 5.5 | 0 |
| | | SD | 0.06 | 0.1 | 0 | 0 | 0.01 | 14 | 0.1 | 0.1 | | | | | | |
| 2) PBS/ TDAPS; (290 mosm/kg) | 1 | VEN | 4.95 | 91.5 | 30.4 | 13.1 | 2.41 | 302 | 7.3 | 51.6 | 3.1 | 3.4 | 36 | | | |
| | | SD | 0.03 | 0.1 | 0 | 0.1 | 0.02 | 8 | 0.1 | 0.1 | | | | | | |
| | 1 | AER | 4.88 | 88.4 | 31.9 | 13.1 | 2.45 | 324 | 6.5 | 55.4 | | | | | | |
| | | SD | 0.06 | 0.1 | 0 | 0.1 | 0.02 | 5 | 0.1 | 0.9 | | | | | | |
| | 2 | VEN | 4.89 | 95.6 | 28.9 | 13.6 | 2.41 | 300 | 6.1 | 56.5 | | | | 4.1 | 45 | 18 |
| | | SD | 0.04 | 0.2 | 0.1 | 0 | 0.02 | 6 | 0.1 | 1.3 | | | | | | |

*Each sample was aspirated 5 times.
Abbreviations: Glut: glutaraldehyde; SDS: sodium dodecyl sulfate; Ven: Venous blood sample; Aer: Aerated blood sample; SD: standard deviation; RBC: Red Blood Cell; MCV: Mean Cell Volume; CHCM: Cellular Hb Concentration Mean; RDW; Red Cell Distribution Width; HDW: Hemoglobin Distribution Width; PLT: Platelets; MPV: Mean Platelet Volume; PDW: Platelet Distribution Width; ΔMCV: Difference in Mean Cell Volume;

Example 9

Table 7 provides a summary of the properties of three reagents compared with respect to various parameters as presented in the table. The three reagents were: (1) H*™RBC diluent comprising glutaraldehyde and SDS, pH 7.2–7.5, 290 mosm/kg; (2) Reagent comprising PBS and TDAPS, pH 7.3, 290 mosm/kg, and (3) Reagent of the present invention comprising bicarbonate (25–28 mM), TDAPS, NaCl, pH 7.3, 289–290 mosm/kg (no glutaraldehyde). Reagent 1 corresponds to Reagent A of Table 5 and Reagent 3 corresponds to Reagent B of Table 5 as assayed in Examples 6, 7 and 8.

In Table 7, Reagent 1 represents a conventional "sphere and fixative" reagent which utilizes SDS to sphere red blood cells and glutaraldehyde to "fix" or chemically crosslink red blood cells (Kim and Ornstein, 1983, *Cytometiy*, 3:419–427). This reagent "locks-in" the sample handling effects of cell shrinkage caused by sample aeration and cell swelling due to the buildup of metabolic $CO_2$ produced during sample storage. Further, the stability of Reagent 1, and similar reagents, is limited by glutaraldehyde to approximately one year due to the intermolecular aldol condensation of the aldehyde in this reagent.

By comparison, Reagent 2, which is comprised of PBS and is free of glutaraldehyde, partially reversed both the sample handling effects (i.e., aeration induced cell shrinkage (36%); and storage induced cell swelling (18%)). Reagent 2 is pH stable to the air.

Reagent 3, which is free of glutaraldehyde and contains bicarbonate, totally reverses the aeration effect and causes a 50% reversal of the storage effect. As described herein, this reagent is employed in conjunction with a collapsible and flexible storage container which contains a barrier to $CO_2$.

Data for MCV, a parameter which typically varies with sample handling, was obtained using the above-listed three reagents, which were analyzed for the ability to reverse the storage related swelling of red cells in the blood samples (e.g., storage swelling induced by storage at room temperature for 24 hours). The difference between the mean MCV's for Day 2 and Day 1 were obtained, and then normalized as a percentage of Day 1. The normalized data were then compared with the glutaraldehyde-containing reagent ("H*™RBC Diluent") which was defined as 0% reversal. Reagent 2 reversed 18% of the swelling of red cells in the three samples. Reagent 3, reversed swelling by 50%. Consequently, a comparison of the effects of Reagents 2 and 3 with those of Reagent 1 containing glutaraldehyde demonstrates that deletion of the glutaraldehyde (with and without the addition of $NaHCO_3$ to the reagent) provided a benefit with respect to reversal of storage-related-swelling caused by the RBC reagent.

The results relating to reversal of the aeration effect (aeration-induced shrinkage) is also summarized in Table 7. Analogous to the swelling results, the venous/aerated MCV difference was obtained and then normalized as a percentage of venous MCV. The normalized data were then compared, with Reagent 1 (H*™RBC Diluent) defined as 0% reversal. As observed in Table 7, Reagent 2 with no added bicarbonate reversed 35% of the aeration effect. Reagent 3 completely reversed the aeration effect. Consequently, the key to complete reversal of the aeration effect is the presence of bicarbonate in the reagent. The partial reversal ability of Reagent 2 to reverse storage related swelling is probably related to the presence of about 0.1–0.2 mM $HCO_3^-$ in this reagent which is due to equilibration of the reagent with atmospheric $CO_2$. This behavior is presumably related to the data presented in FIG. 2, in which an analogous reagent was able to completely reverse the aeration shrinking effect after a significant time period, i.e., about 300 seconds.

TABLE 7

| Reagent Composition | pH | Glutaraldehyde | Aeration shrinkage | Storage swelling | Stability limitation |
|---|---|---|---|---|---|
| 1. Glutaraldehyde/ SDS/290 mosm/Kg ("H* ™ RBC Diluent") | 7.2–7.5 | yes | 2 to 5 fL | 5 to 10 fL | glutaraldehyde |

TABLE 7-continued

| Reagent Composition | pH | Glutaraldehyde | Aeration shrinkage | Storage swelling | Stability limitation |
|---|---|---|---|---|---|
| 2. PBS/TDAPS/290 mosm/Kg* | 7.3 | no | 36% reversal | 18% reversal | pH stable |
| 3. NaHCO$_3$/NaCl/ TDAPS/290 mosm/ Kg acccording to the present invention | 7.3 | no | complete reversal | 50% reversal | pH** |

*Reagent 2 contains no added bicarbonate, but contains ~0.1–0.2 mM HCO$_3$ due to equilibration of CO$_2$ from air.
**As described herein in accordance with the present invention, the pH of this reagent can be stabilized by means of a special flexible multilayer package with low CO$_2$ permeability.

Example 10

This example presents data showing the pH stability of glutaraldehyde-free, bicarbonate-containing reagent composition according to the present invention stored for over 3.5 years in various containers (Table 8).

The reagent composition was prepared as follows: 7.02 grams of NaCl (Mallinckrodt) and 2.10 grams of Na Bicarbonate (NaHCO$_3$, Fisher) were dissolved in 850 ml of MilliQ-filtered water. 200 $\mu$L Proclin 150 and 224 $\mu$L of a TDAPS stock solution (35.0 g/L tetradecylammoniopropanesulfonate/10.0 ml of MQ water), (Boehringer Mannheim), were added. The pH was assayed (pH 8.2) and was adjusted to 7.33 by adding a few drops of 6 N HCl. The osmolality of the solution (320+/−1 mosm/Kg) was assayed and adjusted to 288+−1 mosm/Kg by the addition of 88 ml MQ water.

TABLE 8 pH Stability of Bicarbonate-Containing, Glutaraldehyde-Free Reagent Composition of the Present Invention after Long-Term Storage in Various Containers

| Test Date | Saranex 15 barrier bag | 500 ml HDPE BTL ½ full | 250 ml HDPE BTL full | 125 ml glass BLT full | 500 ml glass BTL ½ full | Electrode |
|---|---|---|---|---|---|---|
| Nov 6, 1995 | 7.60 | 7.46 | N/A | 7.52 | 7.50 | Radiometer* |
| Dec 12, 1995 | 7.66 | 7.79 | 8.01 | 8.98 | 8.59 | Radiometer |
| Jan 29, 1996 | 7.60 | 8.23 | 8.08 | 9.12 | 9.07 | Radiometer |
| Feb 29, 1996 | 7.57 | 8.30 | 8.18 | 9.12 | 9.19 | Radiometer |
| Apr 8, 1996 | 7.67 | 8.48 | 8.35 | 9.22 | 9.20 | Radiometer |
| May 8, 1996 | 7.68 | 8.47 | 8.40 | 9.18 | 9.17 | Radiometer |
| Jun 7, 1996 | 7.68 | 8.51 | 8.45 | 9.18 | 9.16 | Radiometer |
| Jul 8, 1996 | 7.73 | 8.54 | 8.5 | 9.23 | 9.20 | Radiometer |
| Aug 14, 1996 | 7.71 | 8.65 | 8.58 | 9.29 | 9.21 | Radiometer |
| Sep 17, 1996 | 7.74 | 8.66 | 8.59 | 9.29 | 9.19 | Radiometer |
| Oct 15, 1996 | 7.76 | 8.70 | 8.62 | 9.28 | 9.20 | Radiometer |
| Dec 6, 1996 | 7.84 | 8.78 | 8.67 | 9.37 | 9.24 | Radiometer |
| Jan 9, 1997 | 7.81 | 8.81 | 8.80 | 9.30 | 9.26 | Radiometer |
| Nov 24, 1997 | 7.99 | 8.79 | 8.72 | 9.22 | 9.16 | Radiometer |
|  | 8.03 | 8.43 | 8.79 | 9.33 | 9.23 | Microprobe |
| May 11, 1999 | 8.20 | 8.97 | 8.93 | 9.37 | 9.32 | Radiometer |

*Radiometer (America) is both the company and product name.

As presented in Table 8, on Nov. 6, 1995, 950 ml of a NaHCO$_3$/TDAPS/NaCl (no glutaraldehyde) reagent, pH 7.33, according to the present invention was prepared and then manually loaded into a barrier bag by syringe. During the loading operation, some contact of the reagent with air occurred and the pH rose to 7.6, which was considered to be the actual starting pH of the reagent. Storage of the reagent in the CO$_2$ barrier bag according to the present invention was associated with a small pH rise—after 7 months, the pH rose 0.08 units; and after 14 months, the rise was 0.24 pH units, as measured by pH electrode and with a microelectrode pH probe. For these types of measurements, the bag was squeezed to fill the straw and the pH microprobe was inserted into the straw. The results show that the barrier bag did minimize the loss of HCO$_3$, in the form of CO$_2$, to the air.

In contrast, storage of the same reagent composition in a bottle made of HDPE led to a pH rise of 1.1 pH units during the same time period, probably due to CO$_2$ leakage through the plastic to the air. Finally, storage of this reagent composition in the glass bottle led to the largest change over the time period, i.e., a rise of 1.74 pH units. Since glass is impermeable to CO$_2$, the pH rise was possibly caused by an uncharacterized interaction of the reagent with the specific type of glass in the bottle wall. Thus, the reagent composition stored in the bag according to the present invention had a lower pH, and hence higher CO$_2$ concentration than the reagents in the bottle, and the delta (pH change) over 2 years' storage at room temperature was +0.4 pH.

Of particular interest, after 3.5 years of storage in the collapsible bag, the bicarbonate-containing reagent of the present invention had a pH of 8.2. Consequently, over this time period, the pH rose 0.60 pH units. Although the reagent did lose some bicarbonate, it had retained function (See. Example 12).

Example 11

Experiments were performed to test the effect of variation of NaHCO$_3$ concentration in the glutaraldehyde-free reagent. In the present Example 11, variation of reagent NaHCO$_3$ concentration was assessed with respect to ability to reverse the effect of blood sample aeration.

"Reagent A" containing 27 mM NaHCO$_3$, pH 7.30, 289+/−1 mosm/kg, 8.3 mg/L TDAPS and 0.4 ml/L Proclin 300 was prepared. "Reagent D" was prepared as a diluent for Reagent A and contained PBS (Sigma), pH 7.35, 292+/−1 mosm/kg, and 0.4 ml/L Proclin 300. Reagent A was diluted 10-fold with Reagent D to produce Reagent B, which then contained 2.7 mM NaHCO$_3$, pH 7.30, 290 mosm/kg. Similarly, "Reagent C" was prepared by a 20-fold dilution of Reagent A with Reagent D.

Blood was aerated for 24 hours as described in Example 1, and then was returned to its original tube. A pair of venous and aerated blood samples from the same donor was assayed in triplicate using the Bayer H*1 ™ System with the glutaraldehyde- and SDS-containing RBC Diluent reagent and also with Reagents A, B, C and D. (See Table 9).

With the glutaraldehyde- and SDS-containing reagent, the effect of sample aeration caused the MCV to diminish 2.7 fL, which was equivalent to 3.1% relative to the venous sample. By contrast, with Reagent A (27 mM $NaHCO_3$), the MCVs of the venous and aerated samples differed by only 0.33%. With Reagent B (2.7 mM $NaHCO_3$), the venous and aerated samples differed by 0.55%. With Reagent C (1.4 mM $NaHCO_3$), the venous and aerated samples differed by 0.66%. Finally, with Reagent D (no added $NaHCO_3$), the MCVs of the venous and aerated samples differed by 2.9%, which was essentially the same as the value obtained for the reagent containing glutaraldehyde and SDS.

Both Reagent D and the reagent containing glutaraldehyde and SDS were assumed to contain ~0.1–0.2 mM bicarbonate as a result of equilibration of the formulation water with $CO_2$ in the air. The experiments described in Example 11 thus illustrate that for the glutaraldehyde-free reagent, the aeration effect can be largely eliminated over a range of ~1.4 to 27 mM bicarbonate.

TABLE 9

| Reagent | Glutaraldehyde | $HCO_3$, mM | MCV Venous | MCV Aerated | ΔMCV | % Relative Difference |
|---|---|---|---|---|---|---|
| Glut-SDS | Yes | 0.2 | 86.9 | 84.2 | 2.7 | 3.1 |
| A | No | 27.0 | 90.7 | 91.0 | 0.3 | 0.33 |
| B | No | 2.7 | 90.5 | 90.0 | 0.5 | 0.55 |
| C | No | 1.4 | 90.4 | 89.8 | 0.6 | 0.66 |
| D | No | 0.2* | 90.8 | 88.2 | 2.6 | 2.9 |

*0.2 mM $HCO_3^-$ is the concentration of $HCO_3^-$ caused by entry of $CO_2$ from the air into the reagent buffered at pH 7.3.

Example 12

After 3.5 years of storage on the bench, the $HCO_3^-$-containing reagent was connected to a Bayer H*1™ Hematology System and tested to determine its effectiveness in reversing aeration-induced shrinkage of red blood cells. In addition, reagent stored in the flexible collapsible bag according to the present invention was also tested for its ability to reverse storage induced swelling of red blood cells.

Freshly drawn blood, anticoagulated with $K_3$EDTA, was aerated by the method described in Example 1. The aerated blood was returned to its original tubes. Venous and aerated blood samples from the same donor were assayed on the Bayer H*1™ System using the both the glutaraldehyde and SDS-containing RBC reagent and also the glutaraldehyde-free, bicarbonate and TDAPS-containing reagent of the present invention. The reagent in the reagent storage carrier bag was connected to the system in the following manner: the reagent straw of the bag was connected to the RBC reagent straw of the System using a short (i.e., ½% inch long) piece of tubing which acted as a sleeve. The two reagents were primed 10 times prior to each run. Each sample was aspirated 10 times via the manual closed tube sampler. The data are summarized in Tables 10A and 10B.

The results of the assays showed that with the glutaraldehyde- and SDS-containing reagent (Table 10A), the effect of sample handling caused the MCV of the aerated sample to decrease by 3.0 fL (or an ~3.4% difference relative to the venous sample). In contrast, with the glutaraldehyde-free/bicarbonate/TDAPS reagent according to the present invention (Table 10B), the % difference between the venous and aerated blood samples was reduced to ~0.11%, which is within the experimental error of the measurement. Therefore, the bicarbonate reagent of the invention completely eliminated the aeration-induced sample handling effect after this reagent had been stored for well over 3 years in the flexible, collapsible barrier bag.

TABLE 10A

H* ™ RBC Reagent Containing Glutaldehyde

| Blood | RBC | MCV | CHCM | RDW | HDW |
|---|---|---|---|---|---|
| Venous | 3.97* | 87.5 | 33.1 | 13.5 | 2.31 |
| sd** | 0.03 | 0.05 | 0.01 | 0.1 | 0.01 |
| Aerated | 3.94 | 84.5 | 35.1 | 13.6 | 2.37 |
| sd | 0.03 | 0.1 | 0.1 | 0.1 | 0.01 |

TABLE 10B

Bicarbonate Reagent in Flexible Barrier Bag

| Blood | RBC | MCV | CHCM | RDW | HDW |
|---|---|---|---|---|---|
| Venous | 3.99* | 87.1 | 33.2 | 13.7 | 2.22 |
| sd** | 0.03 | 0.1 | 0.0 | 0.1 | 0.02 |
| Aerated | 3.98 | 87.0 | 33.3 | 13.7 | 2.20 |
| sd | 0.03 | 0.3 | 0.2 | 0.1 | 0.03 |

*All data points are the mean of 10 replicates obtained from one blood sample.
**standard deviation.

A summary of the MCV data presented in Tables 10A and 10B is as follows:

| Blood | H* ™ RBC Rgt w/Glut. | Bicarb.-Containing Rgt in Bag |
|---|---|---|
| Venous | 87.5 +/- 0.07 | 87.5 +/- 0.13 |
| Aerated | 84.5 +/- 0.12 | 87.0 +/- 0.34 |
| % Change MCV | 3.42% | 0.11% |

H*™MRBC Rgt W/Glut (H*™RBC Reagent containing Glutaraldehyde) is the glutaraldehyde- and SDS-containing reagent;

Bicarb.-Containing Rgt in Bag (Bicarbonate-Containing Reagent in Flexible Barrier Bag) is the glutaraldehyde-free, bicarbonate-containing reagent stored in the $CO_2$ barrier bag according to the present invention.

Twenty-four hours after the above experiment was performed, the same reagents were employed to determine the utility of the bicarbonate- and TDAPS-containing reagent to reverse the storage-induced swelling of red blood cells. (See Tables 11A and 11B). The blood samples stored for 24 hours at room temperature are termed "aged" blood samples. With the glutaraldehyde-SDS RBC reagent, storage of blood on the bench overnight, i.e., for 24 hours, caused the MCV of the venous sample to increase 7.5 fL (or 8.6% relative to the MVC of the fresh venous sample). The bicarbonate and TDAPS-containing reagent according to the present invention yielded an increase of 3.8% relative to the fresh venous blood. Consequently, the bicarbonate and TDAPS-containing reagent of the present invention was able to reverse 56% of the 24 hour sample storage effect.

For the aerated aged blood samples, 24 hours of storage on the bench was associated with a 7.5% increase in MCV as determined with the glutaraldehyde and SDS-containing reagent. In contrast, the % increase was reduced to 2.9% with the bicarbonate and TDAPS-containing reagent. This represents a 63% reversal of the 24 hour sample storage effect.

TABLE 11A

H* ™ RBC Reagent Containing Glutaldehyde

| Blood | RBC | MCV | CHCM | RDW | HDW |
|---|---|---|---|---|---|
| Venous virgin, aged | 4.00 | 95.0 | 29.9 | 13.8 | 2.27 |
| sd | 0.02 | 0.09 | 0.0 | 0.1 | 0.01 |
| Aerated | 3.97 | 90.8 | 31.8 | 13.7 | 2.30 |
| sd | 0.01 | 0.2 | 0.0 | 0.1 | 0.02 |

TABLE 11B

Bicarbonate Reagent in Collapsible Barrier Bag

| Blood | RBC | MCV | CHCM | RDW | HDW |
|---|---|---|---|---|---|
| Venous | 3.99 | 90.4 | 31.3 | 14.2 | 2.36 |
| sd | 0.02 | 0.2 | 0.1 | 0.1 | 0.01 |
| Aerated | 3.96 | 89.4 | 31.8 | 13.9 | 2.27 |
| sd | 0.02 | 0.19 | 0.07 | 0.16 | 0.01 |

A summary of the results shown in Tables 11A and 11B demonstrating % reversal of swelling due to overnight (i.e., 24 hour) storage of blood samples on the bench (i.e., at room temperature) is presented below:

For venous blood with standard glutaraldehyde-containing reagent, the swelling overnight was 8.6% ([95.0–87.5/87.5]×100=8.6%) versus 3.8% swelling overnight with the bicarbonate-containing reagent of the invention ([90.4–87.1/87.1]×100=3.8%). For aerated blood samples there was 7.5% swelling overnight with the glutaraldehyde-containing reagent ([90.8–84.5/84.5]×100=7.5%) versus 2.8% swelling with the glutaraldehyde-free, bicarbonate-containing reagent of the invention ([89.4–87.0/87.0]×100=2.8%). Therefore, for venous aged blood, the bicarbonate-containing reagent stored in the flexible barrier bag reversed 56% of the swelling; while for aerated aged blood, there was a 63% reversal of swelling.

After 3.5 years of storage in the flexible, multilayer barrier bag, the reagent comprising bicarbonate/TDAPS/290 mOsm/Kg retained functional performance on the H™*1 hematology analyzer. This reagent was still able to completely reverse aeration-induced shrinkage of red blood cells, and also reduce storage-related swelling of red blood cells by 56%. Such properties of this reagent demonstrate its long-term stability and functional performance, and show that the properties of the reagent are virtually unchanged compared with fresh reagent. (See Examples 5,6 and 9, and Table 7).

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of reversing or reducing aeration induced cell shrinkage and storage induced swelling of cells in a whole blood sample to be analyzed on a hematology analyzer, comprising:
    a) mixing an analyzable portion of the blood sample with a reagent diluent composition comprising (i) bicarbonate in an amount of about 1.4 to about 35 mmole/L to provide bicarbonate to the diluted sample to match the bicarbonate concentration in venous whole blood and (ii) a surfactant in an amount of about 7.5 to about 8.5 mg/L to sphere blood cells in the sample, and having a pH of about 7.2 to about 7.5, to produce a reagent mixture; said reagent diluent composition being stored prior to use in an air-impermeable container comprised of a flexible collapsible multilayer material that is impermeable to diffusion of carbon dioxide, whereby the bicarbonate concentration and reagent diluent pH are maintained over time in said air-impermeable container, said container being attachable to the hematology analyzer; and
    b) analyzing the reagent mixture of (a) on the hematology analyzer, whereby the aeration induced cell shrinkage and the storage induced swelling of blood cells mixed with said reagent diluent composition are reversed or reduced; wherein aeration induced cell shrinkage is established by measuring mean cell volume (MCV), and said reagent diluent composition stored in said air impermeable container reverses the effect of blood sample aeration on mean cell volume (MCV) by 100% at room temperature; and further wherein said reagent diluent composition stored in said air-impermeable container reverses about 50% of swelling of a blood sample stored overnight at room temperature.

2. A method of reversing or reducing aeration induced cell shrinkage and storage induced swelling of cells in a whole blood sample to be analyzed on a hematology analyzer, comprising:
    a) mixing an analyzable portion of the blood sample with a reagent diluent composition comprising (i) bicarbonate in an amount of from about 25 mMol/L to about 28 mMol/L to provide bicarbonate to the diluted sample to match the bicarbonate concentration in venous whole blood and (ii) a surfactant in an amount of about 7.5 mg/L to about 8.5 mg/L to sphere blood cells in the sample, and having a pH of about 7.2 to about 7.5, to produce a reagent mixture; and
    b) analyzing the reagent mixture of (a) on the hematology analyzer, whereby the aeration induced cell shrinkage and the storage induced swelling of blood cells mixed with said reagent diluent composition are reversed or reduced; wherein aeration induced cell shrinkage is established by measuring mean cell volume (MCV), and said reagent diluent composition reverses the effect of blood sample aeration on mean cell volume (MCV) by 100% at room temperature; and further wherein said reagent diluent composition reverses about 50% of swelling of a blood sample stored overnight at room temperature.

3. The method according to claim 2, further wherein, in step a), the reagent diluent composition is stored prior to use in an air-impermeable container comprised of a flexible collapsible multilayer material that is impermeable to diffusion of carbon dioxide, and further wherein the bicarbonate concentration and reagent diluent pH are maintained over time in said air-impermeable container, said container being attachable to the hematology analyzer.

4. The method according to claim 3 or claim 1, wherein the reagent diluent composition maintains the bicarbonate concentration in the air-impermeable flexible collapsible multilayer container for about 3.5 years.

5. The method according to claim 1, wherein the bicarbonate concentration in said reagent diluent composition of a) is in the range of about 2.8 mMol/L to 28 mMol/L.

6. The method according to claim 2 or claim 1, wherein the surfactant is a zwitterionic surfactant.

7. The method according to claim 6, wherein the zwitterionic surfactant is selected from the group consisting of betaines, carboxybetaines, sulfobetaines (sultanes), amidobetaines and sulfoamidobetaines.

8. The method according to claim 6, wherein the zwitterionic surfactant is selected from the group consisting of n-alkyldimethylammonio methane carboxylate (DAMC), n-alkyldimethylammonio ethane carboxylate (DAEC) and n-alkyldimethylammonio propane carboxylate (DAPC).

9. The method according to claim 6, wherein the zwitterionic surfactant is selected from the group consisting of n-alkylsultaine, n-alkyl dimethylammonio alkyl sulfonate, n-alkyl dimethylammonio methane sulfonate (DAMS), n-alkyl dimethylammonio ethane sulfonate (DAES), n-alkyl dimethylammonio propane sulfonate (DAPS) and n-alkyl dimethylammonio butane sulfonate (DABS).

10. The method according to claim 7, wherein the zwitterionic surfactant is laurylamidopropylbetaine (LAB).

11. The method according to claim 6, wherein the zwitterionic surfactant is N-tetradecyl-N-alkyl dimethylammonio propane sulfonate (TDAPS).

12. The method according to claim 6, wherein the zwitterionic surfactant is 3-[(3-cholamidopropyl)dimethylammonio]-1-propanesulfonate (CHAPS) or 3-[(3-cholamidopropyl)dimethylammonio]-2-hydroxy-1-propanesulfonate (CHAPSO).

13. The method according to claim 2 or claim 1, wherein the surfactant is a nonionic surfactant.

14. The method according to claim 13, wherein the nonionic surfactant is an alkylglycoside.

15. The method according to claim 14, wherein the alkylglycoside is selected from the group consisting of n-dodecyl-β-D-maltoside, n-tetradecyl-β-D-maltoside and n-tetradecyl-β-D-glucoside.

16. The method according to claim 2 or claim 1, wherein the reagent diluent composition of a) has a pH of about 7.3 to 7.4.

17. The method according to claim 2 or claim 1, wherein said reagent diluent composition of a) contains no crosslinking agent or fixative.

18. The method according to claim 2 or claim 1, wherein said reagent diluent composition optionally contains a chelating agent.

19. The method according to claim 18, wherein said chelating agent is selected from the group consisting of ethylenediaminetetraacetic acid (EDTA), salts of ethylenediaminetetraacetic acid (EDTA), potassium ethylenediaminetetraacetic acid ($K_3$EDTA) and salts of potassium ethylenediaminetetraacetic acid ($K_3$EDTA).

20. The method according to claim 2 or claim 1, wherein said reagent diluent composition optionally contains an antimicrobial agent.

21. The method according to claim 20, wherein said antimicrobial agent is selected from the group consisting of 2-methyl-4-isothiazoline-3-one; 5-chloro-2-methyl-4-isothiazoline-3-one; N,N'-methylenebis[N'-(1-(hydroxymethyl)-2,5-dioxo-4-imidazolidinyl] urea; and (1-(3-chloroallyl)-3,5,7-triaza-1-azoniaadamantane chloride.

22. The method according to claim 2 or claim 1, wherein said reagent diluent composition of a) comprises an alkali metal salt in an amount effective for maintaining the osmolality of the reagent diluent composition.

23. The method according to claim 22, wherein said alkali metal salt is selected from the group consisting of sodium chloride, potassium chloride and lithium chloride.

24. The method according to claim 2 or claim 1, wherein the osmolality of the reagent diluent composition of a) is about 285 mOsm/kg to about 295 mOsm/kg.

25. The method according to claim 24, wherein the wherein the osmolality of the reagent diluent composition of a) is about 290 mOsm/kg.

26. The method according to claim 3 or claim 1, wherein the flexible collapsible multilayer material of the reagent diluent composition storage container is selected from the group consisting of plastic, low density polyethylene, ethylene vinyl alcohol, poly(vinylidene)dichloride, aluminum and a combination thereof.

27. The method according to claim 26, wherein the low density polyethylene and poly(vinylidene)dichloride layers protect the ethylene vinyl alcohol. layer from exposure to water.

* * * * *